(12) United States Patent
Dwork et al.

(10) Patent No.: US 8,414,645 B2
(45) Date of Patent: Apr. 9, 2013

(54) TRANSCATHETER VALVE DELIVERY SYSTEMS AND METHODS

(75) Inventors: Joshua Dwork, Santa Rosa, CA (US); Patrick E. Macaulay, Windsor, CA (US); Gianfranco M. Pellegrini, Santa Rosa, CA (US); Finn O. Rinne, Santa Rosa, CA (US); Richard Spork, Sebastopol, CA (US); Don Huy Tran, Novato, CA (US); Nathan B. Wiemeyer, Healdsburg, CA (US)

(73) Assignee: Medtronic, Inc., Minneapolis, MN (US)

( * ) Notice: Subject to any disclaimer, the term of this patent is extended or adjusted under 35 U.S.C. 154(b) by 224 days.

(21) Appl. No.: 12/870,567

(22) Filed: Aug. 27, 2010

(65) Prior Publication Data

US 2011/0098805 A1 Apr. 28, 2011

Related U.S. Application Data

(60) Provisional application No. 61/237,373, filed on Aug. 27, 2009.

(51) Int. Cl.
*A61F 2/24* (2006.01)

(52) U.S. Cl.
USPC .......................................................... 623/2.11

(58) Field of Classification Search .................. 623/2.11
See application file for complete search history.

(56) References Cited

U.S. PATENT DOCUMENTS

| | | | |
|---|---|---|---|
| 5,683,451 A | 11/1997 | Lenker et al. | |
| 5,824,041 A | 10/1998 | Lenker et al. | |
| 5,906,619 A | 5/1999 | Olson et al. | |
| 5,957,949 A | 9/1999 | Leonhardt et al. | |
| 2003/0199963 A1 | 10/2003 | Tower et al. | |
| 2005/0038495 A1* | 2/2005 | Greenan | 623/1.11 |
| 2005/0137688 A1 | 6/2005 | Salahieh et al. | |
| 2006/0004439 A1 | 1/2006 | Spenser et al. | |
| 2006/0052867 A1 | 3/2006 | Revuelta et al. | |
| 2006/0259136 A1 | 11/2006 | Nguyen et al. | |
| 2006/0265056 A1 | 11/2006 | Nguyen et al. | |
| 2007/0005131 A1 | 1/2007 | Taylor | |
| 2007/0088431 A1 | 4/2007 | Bourang et al. | |
| 2007/0239266 A1 | 10/2007 | Birdsall | |
| 2007/0239269 A1 | 10/2007 | Dolan et al. | |
| 2008/0065011 A1 | 3/2008 | Marchand et al. | |
| 2008/0082165 A1 | 4/2008 | Wilson et al. | |
| 2008/0147160 A1 | 6/2008 | Ghione et al. | |
| 2008/0147181 A1 | 6/2008 | Ghione et al. | |
| 2008/0188928 A1 | 8/2008 | Salahieh et al. | |
| 2009/0054976 A1 | 2/2009 | Tuval et al. | |

(Continued)

FOREIGN PATENT DOCUMENTS

| | | |
|---|---|---|
| EP | 2074964 A1 | 7/2009 |
| GB | 2433700 | 7/2007 |

(Continued)

*Primary Examiner* — Melanie Tyson

(57) ABSTRACT

Delivery devices and methods for percutaneously delivering a prosthetic valve to the heart of a patient. These prosthetic valves may be configured to provide complimentary features that promote optimal placement of the prosthetic valve in a native heart valve, such as the aortic valve, mitral valve, pulmonic valve, and/or tricuspid valve. The delivery device includes a release sheath assembly housed within an outer delivery sheath. A release sheath component of the assembly captures a portion of the prosthetic valve to the delivery device, and effectuates complete release of the prosthetic valve with retraction of the outer sheath.

9 Claims, 16 Drawing Sheets

U.S. PATENT DOCUMENTS

| | | |
|---|---|---|
| 2009/0088836 A1 | 4/2009 | Bishop et al. |
| 2009/0093876 A1 | 4/2009 | Nitzan et al. |
| 2009/0138079 A1 | 5/2009 | Tuval et al. |
| 2009/0171447 A1 | 7/2009 | von Segesser et al. |
| 2009/0177275 A1 | 7/2009 | Case |
| 2009/0281619 A1 | 11/2009 | Le et al. |
| 2010/0094411 A1 | 4/2010 | Tuval et al. |
| 2010/0121434 A1 | 5/2010 | Paul et al. |
| 2010/0191326 A1* | 7/2010 | Alkhatib ............... 623/2.11 |
| 2010/0292782 A1* | 11/2010 | Giannetti et al. ........... 623/2.11 |

FOREIGN PATENT DOCUMENTS

| | | |
|---|---|---|
| WO | WO 00/71059 A1 | 11/2000 |
| WO | 2008/138584 | 11/2008 |
| WO | 2009/091509 | 7/2009 |

* cited by examiner

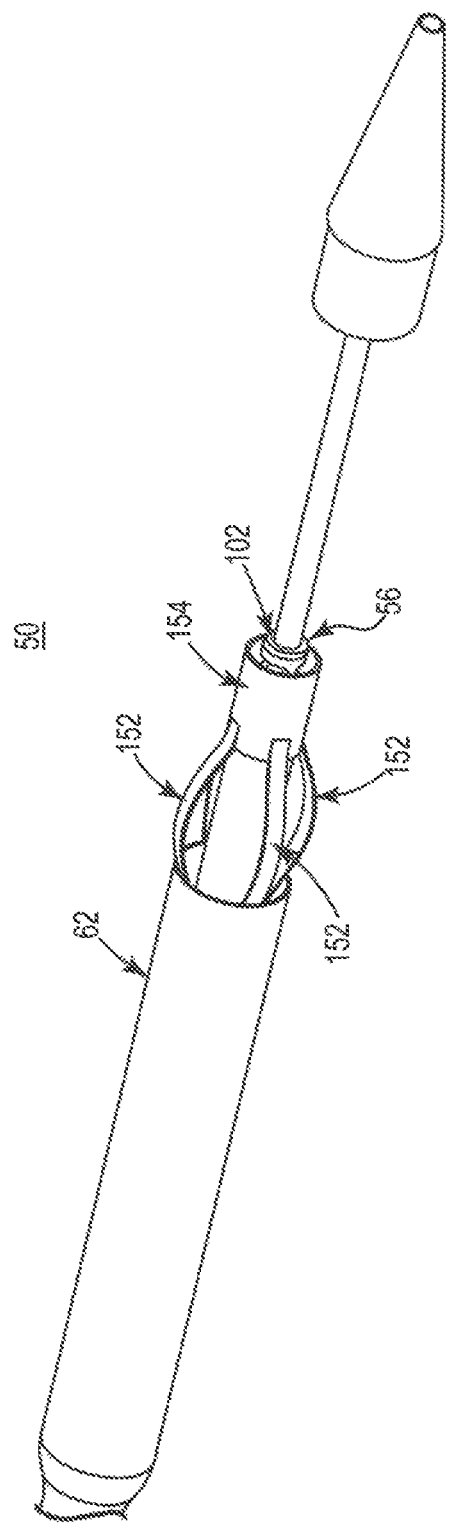

TRANSCATHETER VALVE DELIVERY SYSTEMS AND METHODS

CROSS-REFERENCE TO RELATED APPLICATIONS

This application claims priority under 35 U.S.C. §119(e)(1) to U.S. Provisional Patent Application Ser. No. 61/237,373, filed Aug. 27, 2009, entitled "Transcatheter Valve Delivery Systems and Methods", and the entire teachings of which are incorporated herein by reference.

TECHNICAL FIELD

The present disclosure relates to delivery systems for implanting transcatheter valves. More particularly, it relates to delivery systems and methods of percutaneously implanting prosthetic heart valves.

BACKGROUND

Diseased or otherwise deficient heart valves can be repaired or replaced using a variety of different types of heart valve surgeries. One general type of heart valve surgery involves an open-heart surgical procedure that is conducted under general anesthesia, during which the heart is stopped and blood flow is controlled by a heart-lung bypass machine. This type of valve surgery is highly invasive and exposes the patient to a number of potential risks, such as infection, stroke, renal failure, and adverse effects associated with use of the heart-lung machine, for example.

Due to the drawbacks of open-heart surgical procedures, there has been an increased interest in minimally invasive and percutaneous replacement of cardiac valves. Such surgical techniques involve making a relatively small opening in the skin of the patient into which a valve assembly is inserted and delivered into the heart via a delivery device similar to a catheter. This technique is often preferable to more invasive forms of surgery, such as the open-heart surgical procedure described above.

Various types and configurations of prosthetic heart valves are used in percutaneous valve procedures to replace diseased natural human heart valves. The actual shape and configuration of any particular prosthetic heart valve is dependent to some extent upon the valve being replaced (i.e., mitral valve, tricuspid valve, aortic valve, or pulmonary valve). In general, prosthetic heart valve designs attempt to replicate the function of the valve being replaced and thus will include valve leaflet-like structures used with either bioprostheses or mechanical heart valve prostheses. If bioprostheses are selected, the replacement valves may include a valved vein segment that is mounted in some manner within an expandable stent frame to make a valved stent. In order to prepare such a valve for percutaneous implantation, one type of valved stent can be initially provided in an expanded or uncrimped condition, then crimped or compressed around a balloon portion of a catheter until it is as close to the diameter of the catheter as possible. In other percutaneous implantation systems, the stent frame of the valved stent can be made of a self-expanding material. With these systems, the valved stent is crimped down to a desired size and held in that compressed state with a sheath, for example. Retracting the sheath from this valved stent allows the stent to expand to a larger diameter, such as when the valved stent is in a desired position within a patient. With either of these types of percutaneous stent delivery systems, conventional sewing of the prosthetic heart valve to the patient's native tissue is typically not necessary.

Although there have been advances in percutaneous valve replacement techniques and devices, there is a continued desire to provide different delivery systems for delivering cardiac valves to an implantation site in a minimally invasive and percutaneous manner. There is also a continued desired to be able to reposition and/or retract the valves once they have been deployed or partially deployed in order to ensure optimal placement of the valves within the patient. In addition, there is a desire to provide a valve and corresponding delivery system that provide for easy loading of the valve onto the delivery system and allow for positive release of the valve when it is in its desired position in the patient.

SUMMARY

The delivery devices of the disclosure can be used to deliver replacement valves to the heart of a patient. These replacement heart valves may be configured to provide complimentary features that promote optimal placement of the replacement heart valve in a native heart valve, such as the aortic valve, mitral valve, pulmonic valve, and/or tricuspid valve. In some embodiments, the replacement heart valves of the disclosure are highly amenable to transvascular delivery using a retrograde transarterial approach (either with or without rapid pacing). The methodology associated with the present disclosure can be repeated multiple times, such that several prosthetic heart valves of the present disclosure can be mounted on top of, adjacent to, or within one another, if necessary or desired.

Methods for insertion of the replacement heart valves of the disclosure include delivery devices that can maintain the stent structures in their compressed state during their insertion and allow or cause the stent structures to expand once they are in their desired location. In addition, delivery methods of the disclosure can include features that allow the stents to be retrieved for removal or relocation thereof after they have been at least partially deployed from the stent delivery devices. The methods may include implantation of the stent structures using either an antegrade or retrograde approach. Further, in many of the delivery approaches of the disclosure, the stent structure is rotatable in vivo to allow the stent structure to be adjusted to a desired orientation within the patient.

Some aspects in accordance with principles of the present disclosure relate to a delivery device for percutaneously deploying a stented prosthetic heart valve otherwise including a stent frame to which a valve structure is attached. The delivery device includes a delivery sheath assembly, an inner shaft, a hub, and a release sheath assembly. The delivery sheath assembly terminates at a distal end and defines a lumen. The inner shaft is slidably disposed within the lumen. The hub projects from the inner shaft and is configured to releasably receive a portion of a prosthetic heart valve stent frame, such as one or more posts formed by the stent frame. The release sheath assembly is disposed along the delivery sheath assembly and the inner shaft. In this regard, the release sheath assembly includes a release sheath slidably disposed about the inner shaft. With this construction, the delivery device is configured to provide a loaded state and a deployment state. In the loaded state, the delivery sheath assembly maintains a stented prosthetic heart valve over the inner shaft. Further, the stented prosthetic heart valve is coupled to the hub via the release sheath. In the deployment state, the distal end of the delivery sheath assembly is withdrawn from the prosthetic heart valve, as is the release sheath. In the deployment state, then, the prosthetic heart valve is permitted to release from the hub. In some embodiments, the release sheath assembly is configured to self-retract the release sheath relative to the hub with proximal retraction of the delivery sheath assembly. In other embodiments, the release sheath assembly further includes a mounting base connected to the release sheath by at least one biasing member that can be a leaf spring-like body. With these constructions, the mounting base is fixed to the inner shaft proximal the hub; when the biasing member is constrained with the delivery sheath assembly's lumen, the biasing member is forced to a deflected state, directing the release sheath over the hub. When the biasing member is released from the confines of the delivery sheath assembly, the biasing member self-transitions to a normal state, thereby retracting the release sheath.

Yet other aspects in accordance with principles of the present disclosure relate to a system for replacing a defective heart valve of a patient. The system includes a prosthetic heart valve and the delivery device as described above. The prosthetic heart valve includes a stent frame and a valve structure attached thereto. The stent frame defines a distal region and a proximal region, with the proximal region forming at least one post. In a loaded condition of the system, the post is captured between the release sheath and the hub. Upon retraction of the delivery sheath assembly's distal end proximally beyond the release sheath, the release sheath assembly self-retracts the release sheath, thereby permitting the post to release from the hub.

Yet other aspects in accordance with principles of the present disclosure relates to methods of percutaneously deploying a stented prosthetic heart valve to an implantation site of a patient. A delivery device loaded with a radially expandable prosthetic heart valve having a stent frame and a valve structure is received. The delivery device includes a delivery sheath assembly containing the prosthetic heart valve in a compressed arrangement over an inner shaft in a loaded state of the device. The delivery device further includes a hub projecting from the inner shaft, and a release sheath assembly including a release sheath slidably capturing a post of the stent frame to the hub. The prosthetic heart valve is delivered, in the compressed arrangement, through a bodily lumen of a patient and to the implantation site via the delivery device in the loaded state. The delivery sheath assembly is proximally retracted from the prosthetic heart valve. Finally, the post is permitted to release from the hub in effectuating full deployment, including the release sheath assembly self-retracting the release sheath relative to the hub.

BRIEF DESCRIPTION OF THE DRAWINGS

The present disclosure will be further explained with reference to the appended figures, wherein like structures is referred to by like numerals throughout the several views, and wherein:

FIGS. 10A and 10B are simplified perspective views of the delivery device of FIG. 2A in various stages of transitioning to a deployment state;

DETAILED DESCRIPTION

Figure 1A:
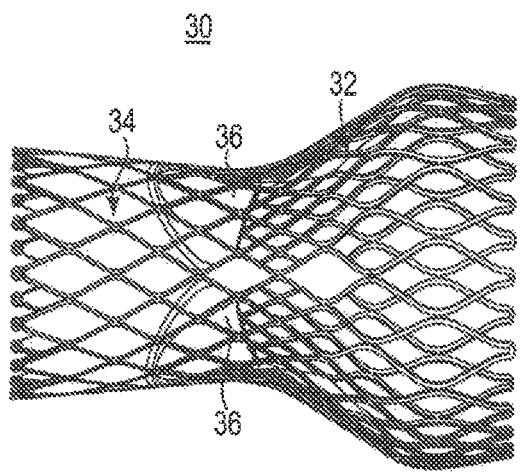
FIG. 1A is a side view of a stented prosthetic heart valve useful with systems and methods of the present disclosure and in a normal, expanded arrangement.

As referred to herein, stented transcatheter prosthetic heart valves useful with and/or as part of the various systems, devices, and methods of the present disclosure may assume a wide variety of different configurations, such as a bioprosthetic heart valve having tissue leaflets or a synthetic heart valve having polymeric, metallic, or tissue-engineered leaflets, and can be specifically configured for replacing any heart valve. Thus, the stented prosthetic heart valve useful with the systems, devices, and methods of the present disclosure can be generally used for replacement of a native aortic, mitral, pulmonic, or tricuspid valve, for use as a venous valve, or to replace a failed bioprosthesis, such as in the area of an aortic valve or mitral valve, for example.

In general terms, the stented prosthetic heart valves of the present disclosure include a stent or stent frame maintaining a valve structure (tissue or synthetic), with the stent having a normal, expanded arrangement and collapsible to a compressed arrangement for loading within a delivery device. The stent is normally constructed to self-deploy or self-expand when released from the delivery device. For example, the stented prosthetic heart valve useful with the present disclosure can be a prosthetic valve sold under the trade name CoreValve® available from Medtronic CoreValve, LLC. Other non-limiting examples of transcatheter heart valve prostheses useful with systems, devices, and methods of the present disclosure are described in U.S. Publication Nos. 2006/0265056; 2007/0239266; and 2007/0239269, the teachings of each which are incorporated herein by reference. The stents or stent frames are support structures that comprise a number of struts or wire portions arranged relative to each other to provide a desired compressibility and strength to the prosthetic heart valve. In general terms, the stents or stent frames of the present disclosure are generally tubular support structures having an internal area in which valve structure leaflets will be secured. The leaflets can be formed from a variety of materials, such as autologous tissue, xenograph material, or synthetics as are known in the art. The leaflets may be provided as a homogenous, biological valve structure, such as porcine, bovine, or equine valves. Alternatively, the leaflets can be provided independent of one another (e.g., bovine or equine pericardial leaflets) and subsequently assembled to the support structure of the stent frame. In another alternative, the stent frame and leaflets can be fabricated at the same time, such as may be accomplished using high-strength nano-manufactured NiTi films produced at Advance BioProsthetic Surfaces (ABPS), for example. The stent frame support structures are generally configured to accommodate at least two (typically three) leaflets; however, stented prosthetic heart valves of the types described herein can incorporate more or less than three leaflets.

Some embodiments of the stent frames can be a series of wires or wire segments arranged such that they are capable of self-transitioning from the compressed or collapsed arrangement to the normal, radially expanded arrangement. In some constructions, a number of individual wires comprising the stent frame support structure can be formed of a metal or other material. These wires are arranged in such a way that the stent frame support structure allows for folding or compressing or crimping to the compressed arrangement in which the internal diameter is smaller than the internal diameter when in the normal, expanded arrangement. In the compressed arrangement, such a stent frame support structure with attached valve leaflets can be mounted onto a delivery device. The stent frame support structures are configured so that they can be changed to their normal, expanded arrangement when desired, such as by the relative movement of one or more outer sheaths relative to a length of the stent frame.

The wires of these stent frame support structures in embodiments of the present disclosure can be formed from a shape memory material such as a nickel titanium alloy (e.g., Nitinol™). With this material, the support structure is self-expandable from the compressed arrangement to the normal, expanded arrangement, such as by the application of heat, energy, and the like, or by the removal of external forces (e.g., compressive forces). This stent frame support structure can also be compressed and re-expanded multiple times without damaging the structure of the stent frame. In addition, the stent frame support structure of such an embodiment may be laser-cut from a single piece of material or may be assembled from a number of different components. For these types of stent frame structures, one example of a delivery device that can be used includes a catheter with a retractable sheath that covers the stent frame until it is to be deployed, at which point the sheath can be retracted to allow the stent frame to self-expand. Further details of such embodiments are discussed below.

Figure 1B:
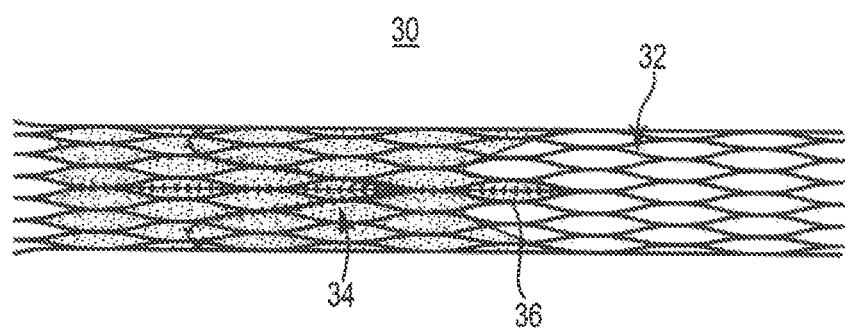
FIG. 1B is a side view of the prosthetic heart valve of FIG. 1A in a compressed arrangement.

With the above understanding in mind, one non-limiting example of a stented prosthetic heart valve 30 useful with systems, devices, and methods of the present disclosure is illustrated in FIG. 1A. As a point of reference, the prosthetic heart valve 30 is shown in a normal or expanded arrangement in the view of FIG. 1A; FIG. 1B illustrates the prosthetic heart valve 30 in a compressed arrangement (e.g., when compressively retained within an outer catheter or sheath). The prosthetic heart valve 30 includes a stent or stent frame 32 and a valve structure 34. The stent frame 32 can assume any of the forms described above, and is generally constructed so as to be self-expandable from the compressed arrangement (FIG. 1B) to the normal, expanded arrangement (FIG. 1A). In other embodiments, the stent frame 32 is expandable to the expanded arrangement by a separate device (e.g., a balloon internally located within the stent frame 32). The valve structure 34 is assembled to the stent frame 32 and provides two or more (typically three) leaflets 36. The valve structure 34 can assume any of the forms described above, and can be assembled to the stent frame 32 in various manners, such as by sewing the valve structure 34 to one or more of the wire segments defined by the stent frame 32.

With the but one acceptable construction of FIGS. 1A and 1B, the prosthetic heart valve 30 is configured for replacing or repairing an aortic valve. Alternatively, other shapes are also envisioned, adapted to the specific anatomy of the valve to be repaired (e.g., stented prosthetic heart valves in accordance with the present disclosure can be shaped and/or sized for replacing a native mitral, pulmonic, or tricuspid valve). With the one construction of FIGS. 1A and 1B, the valve structure 34 extends less than the entire length of the stent frame 32, but in other embodiments can extend along an entirety, or a near entirety, of a length of the stent frame 32. A wide variety of other constructions are also acceptable and within the scope of the present disclosure. For example, the stent frame 32 can have a more cylindrical shape in the normal, expanded arrangement.

Figure 2A:
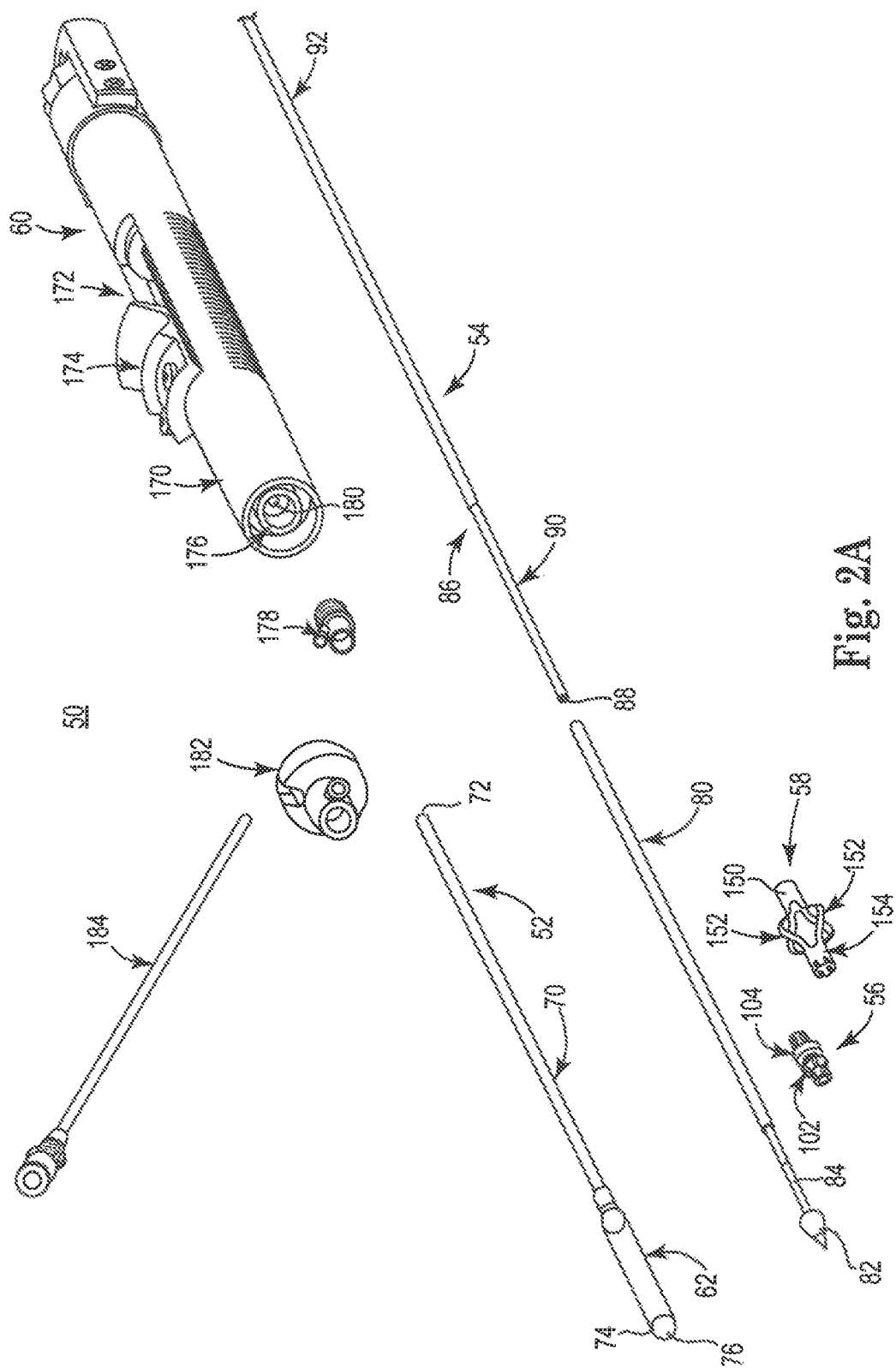
FIG. 2A is an exploded perspective view of a stented prosthetic heart valve delivery device in accordance with principles of the present disclosure.
Figure 2B:
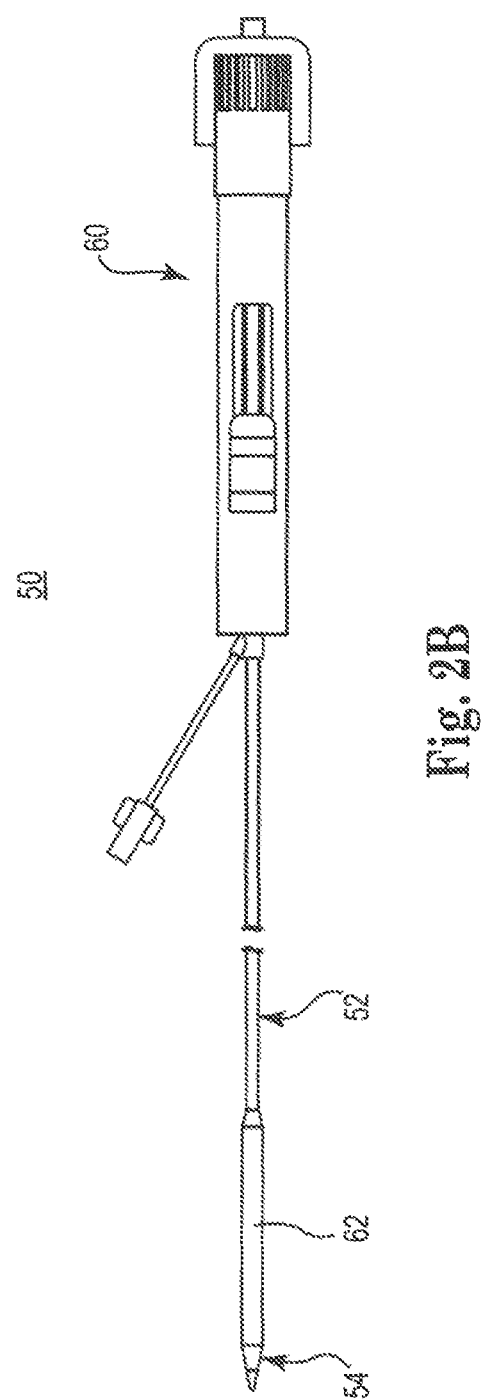
FIG. 2B is a side view of the delivery device of FIG. 2A upon final assembly.

With the above understanding of the stented prosthetic heart valve 30 in mind, one embodiment of a delivery device 50 for percutaneously delivering the prosthesis 30 is shown in FIGS. 2A and 2B. Although the device 50 can be loaded with a stented valve for delivery thereof, such a stented valve is not shown in FIGS. 2A and 2B in order to more clearly illustrate the components of the delivery device 50. The delivery device 50 includes a delivery sheath assembly 52, an inner shaft assembly 54, a retention body or hub 56, a release sheath assembly 58, and a handle 60. Details on the various components are provided below. In general terms, however, the delivery device 50 combines with a stented prosthetic heart valve (not shown) to form a system for repairing a defective heart valve of a patient. The delivery device 50 provides a loaded state in which a stented prosthetic heart valve is coupled to the inner shaft assembly 54 via the hub 56, and compressively retained within a capsule 62 of the delivery sheath assembly 52. The delivery sheath assembly 52 can be manipulated to withdraw the capsule 62 proximally from the prosthetic heart valve via operation of the handle 60, permitting the prosthesis to self-expand and release from the inner shaft assembly 54. The release sheath assembly 58 operates to effectuate this release. Further, the handle 60 can be operated to maneuver the capsule 62 to effectuate a partial deployment state in which a distal region of the prosthetic heart valve is permitted to self-expand, whereas a proximal region of the prosthesis remains coupled to the hub 56.

Various features of the components 52-60 reflected in FIGS. 2A and 2B and described below can be modified or replaced with differing structures and/or mechanisms. Thus, the present disclosure is in no way limited to the delivery sheath assembly 52, the inner shaft assembly 54, the hub 56, the handle 60, etc., as shown and described below. More generally, delivery devices in accordance with the present disclosure provide features capable of compressively retaining a self-deploying, stented prosthetic heart valve (e.g., the capsule 62 in combination with the hub 56/release sheath assembly 58), and a mechanism capable of effectuating partial and full release or deployment of the prosthesis (e.g., retracting the capsule 62 in combination with the release sheath assembly 58).

In some embodiments, the delivery sheath assembly 52 includes the capsule 62 and a shaft 70, and defines proximal and distal ends 72, 74. A lumen 76 is formed by the delivery sheath assembly 52, extending from the distal end 74 through the capsule 62 and at least a portion of the shaft 70. The lumen 76 can be open at the proximal end 72. The capsule 62 extends distally from the shaft 70, and in some embodiments has a more stiffened construction (as compared to a stiffness of the shaft 70) that exhibits sufficient radial or circumferential rigidity to overtly resist the expected expansive forces of the stented prosthetic heart valve (not shown) when compressed within the capsule 62. For example, the shaft 70 can be a polymer tube embedded with a metal braiding, whereas the capsule 62 includes a laser-cut metal tube that is optionally embedded within a polymer covering. Alternatively, the capsule 62 and the shaft 70 can have a more uniform construction (e.g., a continuous polymer tube). Regardless, the capsule 62 is constructed to compressively retain the stented prosthetic heart valve at a predetermined diameter when loaded within the capsule 62, and the shaft 70 serves to connect the capsule 62 with the handle 60. The shaft 70 (as well as the capsule 62) is constructed to be sufficiently flexible for passage through a patient's vasculature, yet exhibits sufficient longitudinal rigidity to effectuate desired axial movement of the capsule 62. In other words, proximal retraction of the shaft 70 is directly transferred to the capsule 62 and causes a corresponding proximal retraction of the capsule 62. In other embodiments, the shaft 70 is further configured to transmit a rotational force or movement onto the capsule 62.

The inner shaft assembly 54 can have various constructions appropriate for supporting a stented prosthetic heart valve within the capsule 62. In some embodiments, the inner shaft assembly 54 include an inner support shaft 80 and a tip 82. The inner support shaft 80 is sized to be slidably received within the lumen 76 of the delivery sheath assembly 52, and is configured for mounting of the hub 56 and the release sheath assembly 58. The inner support shaft 80 can include a distal segment 84 and a proximal segment 86. The distal segment 84 connects the tip 82 to the proximal segment 86, with the proximal segment 86, in turn, coupling the inner shaft assembly 54 with the handle 58. The components 80-86 can combine to define a continuous lumen 88 (referenced generally) sized to slidably receive an auxiliary component such as a guide wire (not shown).

The distal segment 84 can be a flexible polymer tube embedded with a metal braid. Other constructions are also acceptable so long as the distal segment 84 exhibits sufficient structural integrity to support a loaded, compressed stented prosthetic heart valve (not shown), as well as the hub 56 and the release sheath assembly 58 mounted thereto. The proximal segment 86 can include, in some constructions, a leading portion 90 and a trailing portion 92. The leading portion 90 serves as a transition between the distal and proximal segments 84, 86, and thus in some embodiments is a flexible polymer tubing (e.g., PEEK) having an outer diameter slightly less than that of the distal segment 84. The trailing portion 92 has a more rigid construction (e.g., a metal hypotube), adapted for robust assembly with the handle 60. Other materials and constructions are also envisioned. For example, in alternative embodiments, the distal and proximal segments 84, 86 are integrally formed as a single, homogenous tube or solid shaft.

The tip 82 forms or defines a nose cone having a distally tapering outer surface adapted to promote atraumatic contact with bodily tissue. The tip 82 can be fixed or slidable relative to the inner support shaft 80.

Figure 3A:
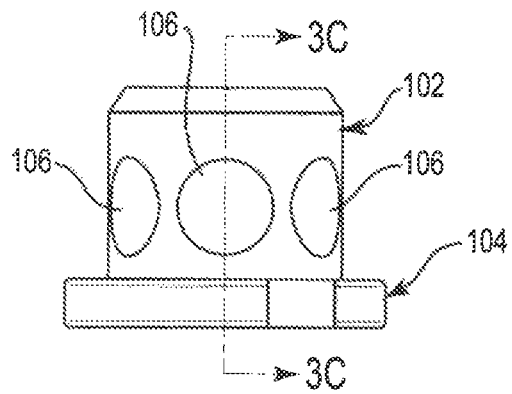
FIG. 3A is a side view of a hub component useful with the delivery device of FIG. 2A.
Figure 3B:
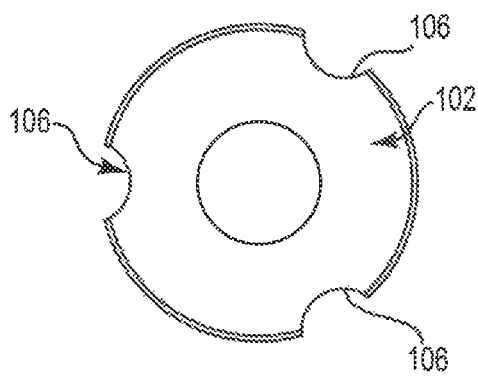
FIG. 3B is an end view of the hub of FIG. 3A.
Figure 3C:
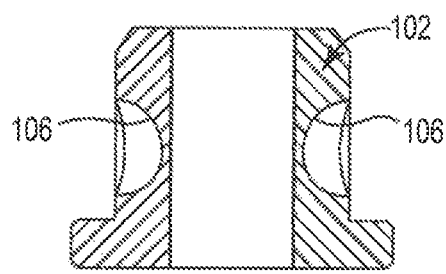
FIG. 3C is a cross-sectional view of the hub of FIG. 3A.

The hub 56 serves to selectively couple corresponding features of the stented prosthetic heart valve (not shown) relative to the inner shaft assembly 54, and can be configured for assembly over the inner support shaft 80. One embodiment of the hub 56 is shown in greater detail in FIGS. 3A-3C. The hub 56 can be used for securing a stent frame to the delivery device 50 until it is desired to release the stent frame within a patient. The hub 56 includes a base cylindrical portion 102 and a flange 104 at one end of the cylindrical portion 102. The flange 104 is at least slightly larger in diameter than the diameter of the cylindrical portion 102. The cylindrical portion 102 includes multiple indentations 106 around its outer periphery. The indentations 106 can be hemispherical or semi-hemispherical, for example, or can have another concave shape. The indentations 106 are recessed areas shaped to engage with outward protrusions of corresponding stent frame wires to aid in securing the stent frame to the delivery device. That is, protrusions can be provided on the end (or posts) of a certain number of stent frame wires, where these protrusions are designed to fit into or engage with the indentations 106 and can also be hemispherical or semi-hemispherical in shape. The number of protrusions that extend from stent frame wires is preferably the same as the number of indentations 106 on the cylindrical portion 102 of the hub 56; however, the number of protrusions provided on a particular stent frame may be different than the number of indentations on the corresponding collar.

The shape of each of the indentations 106 can be the same or similar in shape and size to other indentations of a particular hub. The shape and size of each of the protrusions on the stent frame wires of a stent frame that will engage with the indentations can exactly or closely match the indentation with which it will be engaged. However, the protrusions can be at least slightly smaller and/or differently shaped than the corresponding indentation in which it will be positioned. In any case, each of the protrusions should be able to seat securely within a corresponding indentation for positive engagement between the components. The thickness of each of the stent frame wires that extend from the shaped protrusions can be the same as the rest of the wires of the stent frame, or the thickness can be different. However, in one embodiment, the thickness of the wires will be small enough that when their protrusions are positioned in the indentations 106, the wires do not extend beyond the outer periphery of the flange 104 of the hub 56. In addition, it is contemplated that the protrusions from the stent frame can extend from crowns or other area of a stent wire arrangement, additional wires with protrusions can be provided to extend from an existing stent structure, or other structures can be provided with such protrusions.

Figure 4:
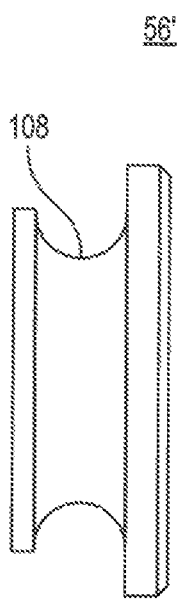
FIG. 4 is a side view of another embodiment hub useful with the delivery device of FIG. 2A.

Another embodiment of a hub 56' useful with the transcatheter stented prosthetic heart valve delivery devices of the present disclosure is shown in FIG. 4. The hub 56' is a generally cylindrical element that includes a radial groove 108 extending around its perimeter. Although the groove 108 of this embodiment extends around an entire perimeter of the hub 56', the hub 56' can instead include multiple grooves spaced from each other.

Returning to FIG. 2A, the hub 56 can assume a wide variety of other forms differing from the above descriptions. For example, the hub 56 can incorporate slots, springs, etc., configured to interface with corresponding feature(s) of the stented prosthetic heart valve 30 (FIG. 1B) (e.g., posts or wire extensions formed by the stent frame 32).

The release sheath assembly 58 is generally constructed to selectively capture the prosthetic heart valve 30 (FIG. 1B) to the hub 56. With this in mind, the release sheath assembly 58 includes a mounting collar or base 150, one or more biasing members 152, and a release sheath 154. In general terms, the mounting base 150 couples the release sheath assembly 58 to the inner support shaft 80. The release sheath 154 is sized to be slidably disposed over the hub 56, with the biasing members 152 serving to bias the release sheath 154 to a longitudinal position relative to the mounting base 150, and thus relative to the hub 56, as described below.

The mounting base 150 can assume various configurations appropriate for non-moveable, fixed mounting to the inner support shaft 80. For example, the mounting base 150 can be a ring or collar that is bonded to the inner support shaft 80. Other structures appropriate for establishing a fixed location relative to the inner support shaft 80 as well as resisting forces generated in or by the biasing member(s) 152 are also envisioned. For example, in other embodiments, the mounting base 150 can be omitted and an end of each of the biasing member(s) 152 opposite the release sheath 154 directly attached to the inner support shaft 80.

The biasing members 152 are leaf spring-like bodies or arms, and are spaced from one another about a periphery of the release sheath 154. In some constructions, the release sheath assembly 58 will include at least two of the biasing members 152, which may be positioned at generally opposite sides of the release sheath 154, if desired, although it is possible that they are positioned different relative to each other. In other constructions, only one of the biasing members 152 is provided. In yet other embodiments, the release sheath assembly 58 includes three or more biasing members 152, and each of the biasing members 152 may be configured the same or differently than the other biasing members 152. Regardless, and as described in greater detail below, the biasing member(s) 152 can have a shape memory attribute, normally or naturally assuming the outwardly curved shape reflected in FIG. 2A, and can be externally forced to deflect to a more straightened shape. Upon removal of the external force, the biasing member(s) 152 self-revert back toward the normal curved shape. Other spring-related shapes or structures are also acceptable.

Figure 5:
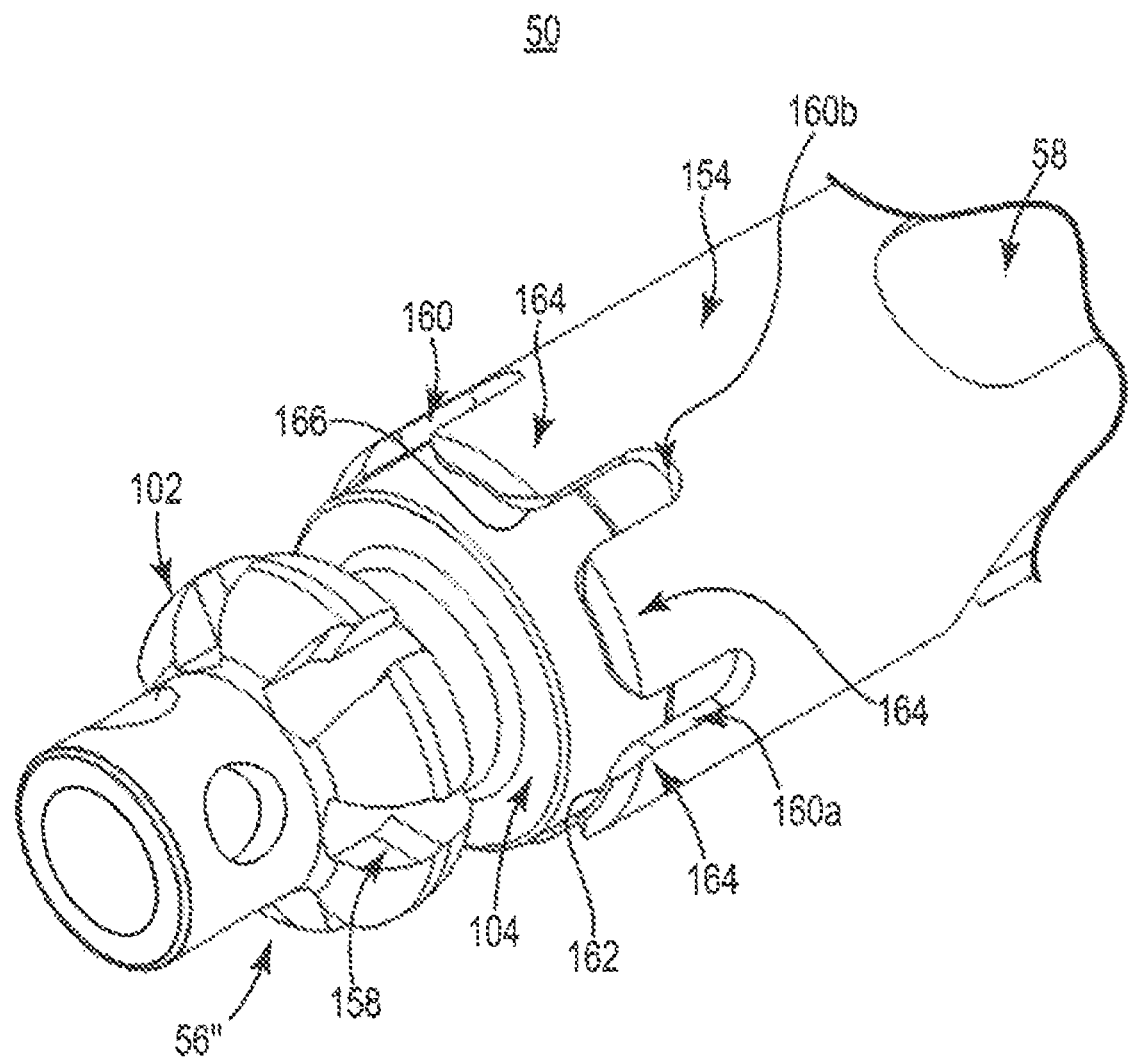
FIG. 5 is a perspective view of a portion of a release sheath assembly component of the delivery device of FIG. 2A.

The release sheath 154 is a tubular body sized to be slidably received over the hub 56, including the flange 104. The release sheath 154 is designed to move freely over the hub 56 due to a gap clearance (e.g., on the order of 0.001 inch or greater) that is provided between the release sheath 154 and the maximum outer diameter of base cylindrical portion 102 and the flange 104. In some constructions, and as best shown in FIG. 5 (that otherwise illustrates the release sheath 154 assembled over the flange 104 of an alternative embodiment hub 56" incorporating longitudinal slots 158 in the base portion 102), the release sheath 154 forms or defines at least one longitudinal notch 160 extending from, and open relative to, a distal end 162 thereof. The release sheath 154 can include a plurality of the notches 160 corresponding with the number of the longitudinal slots 158 provided with the hub 56. The notches 160 can be identical and are arranged relative to a circumference of the release sheath 154 such that each of the notches 160 is longitudinally aligned with a corresponding one of the slots 158 upon assembly of the release sheath 154 over the flange 104. With embodiments in which the release sheath 154 forms two (or more) of the notches 160, two (or more) fingers 164 are formed by or between adjacent ones of the notches 160. For example, a first finger 164a is defined between the first and second notches 160a, 160b. While each of the notches 160 can have a relatively uniform circumferential width, an increased circumferential width is optionally defined immediately adjacent the distal end 162. Alternatively, the notches 160 can have other shapes, and in yet other embodiments are omitted.

Returning to FIG. 2A, the release sheath assembly 58, including the biasing members 152 and/or the release sheath 154, can be made of one of more materials such as metal or polymers (e.g., Nitinol™, stainless steel, Delrin™, and the like). The material(s) have a thickness on the order of 0.002-0.007 inch, for example, although the thickness can be lower or higher than this size range. The release sheath assembly 58 can have a length on the order of 5-15 mm, for example, in order to provide both flexibility and spring-radial strength to the components. The material(s) can have either a closed cell or an open-cell design.

Figure 6A:
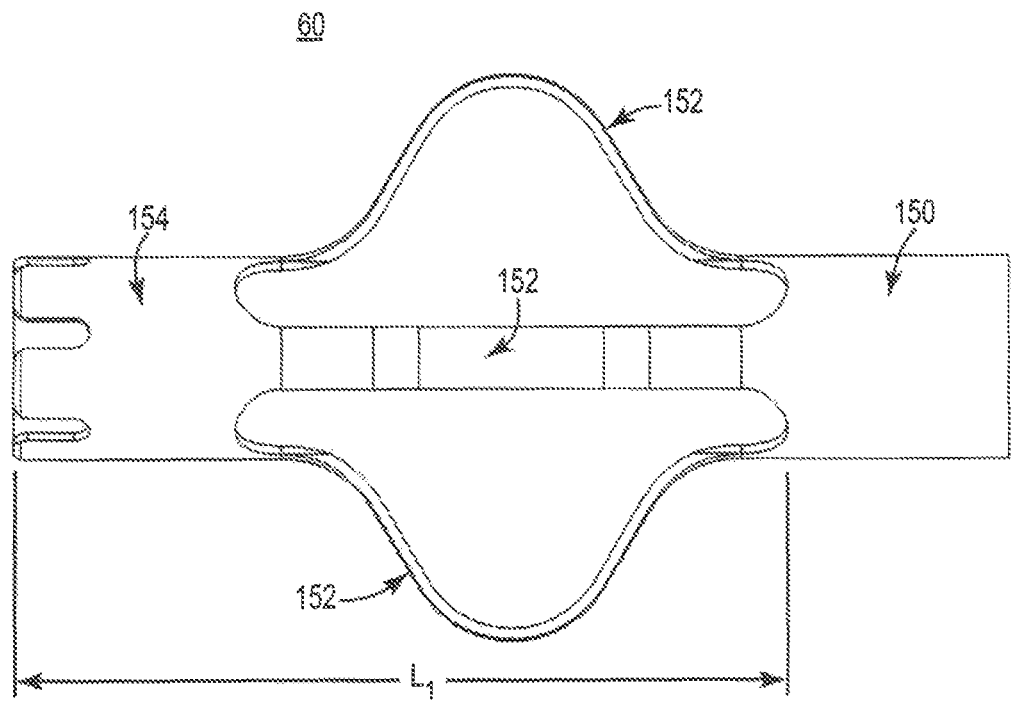
FIG. 6A is a side view of the release sheath assembly component of the delivery device of FIG. 2A and in a normal state.
Figure 6B:
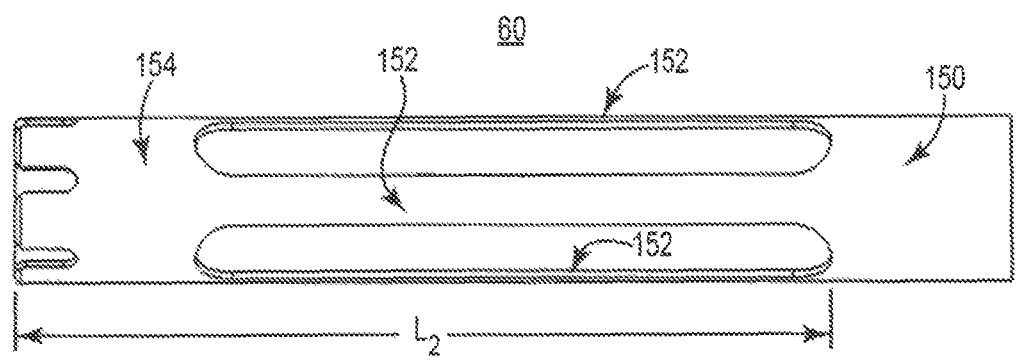
FIG. 6B is a side view of the release sheath assembly of FIG. 6A and in a compressed or deflected state.

Operation of the release sheath assembly 58 in facilitating partial and full deployment of a prosthetic heart valve is based upon a longitudinal position of the release sheath 154 as dictated by biasing members 152. As mentioned above, the biasing members 152 are formed to normally assume the curved shape generally reflected in FIG. 2A. A diameter collectively defined by the biasing members 152 (in their normal state) is greater than a diameter of the delivery sheath assembly lumen 76. Thus, when the release sheath assembly 58 is disposed within the capsule 62 (or within the delivery sheath shaft 70), the biasing members 152 are forced to deflect radially inwardly, effectuating an increase in a longitudinal spacing between the mounting base 150 and the release sheath 154. Upon removal of this external force, the biasing members 152 self-revert back to the natural condition reflected in FIG. 2A, thereby biasing the release sheath 154 to an original longitudinal spacing relative to the mounting base 150. FIGS. 6A and 6B illustrate this relationship in simplified form. FIG. 6A reflects a normal state of the biasing members 152 that establishes a first longitudinal spacing $L_1$ between the mounting base 150 and the release sheath 154. When subjected to a compressive force (e.g., upon insertion within the delivery sheath assembly 52 (FIG. 2A)), the biasing members 152 deflect inwardly as shown in FIG. 6B. Because the mounting base 150 is spatially fixed (i.e., attached to the inner support shaft 80 (FIG. 2A)), the deflected biasing members 152 force the release sheath 154 away from the mounting base 150, to a second longitudinal spacing $L_2$ that is greater than the first longitudinal spacing $L_1$. When the compressive force is removed, the biasing members 152 self-revert back to the arrangement of FIG. 6A, thereby pulling the release sheath 154 back toward the mounting base 150.

Returning the FIG. 2A, the handle 60 generally includes a housing 170 and an actuator mechanism 172 (referenced generally). The housing 170 maintains the actuator mechanism 172, with the actuator mechanism 172 configured to facilitate sliding movement of the delivery sheath assembly 52 relative to the inner shaft assembly 54. The housing 170 can have any shape or size appropriate for convenient handling by a user. In one simplified construction, the actuator mechanism 172 includes a user interface or actuator 174 slidably retained by the housing 170 and coupled to a sheath connector body 176. The proximal end 72 of the delivery sheath assembly 52 is coupled to the sheath connector body 176 (e.g., via an optional mounting boss 178 in some embodiments). The inner shaft assembly 54, and in particular the proximal tube 86, is slidably received within a passage 180 of the sheath connector body 176, and is rigidly coupled to the housing 170. Sliding of the actuator 174 relative to the housing 170 thus causes the delivery sheath assembly 52 to move or slide relative to the inner shaft assembly 54, for example to effectuate deployment of a prosthesis from the inner shaft assembly 54 as described below. Alternatively, the actuator mechanism 172 can assume a variety of other forms differing from those implicated by the illustration of FIG. 2A. Similarly, the handle 60 can incorporated other features, such as a cap 182 and/or a fluid port assembly 184.

Figure 7:
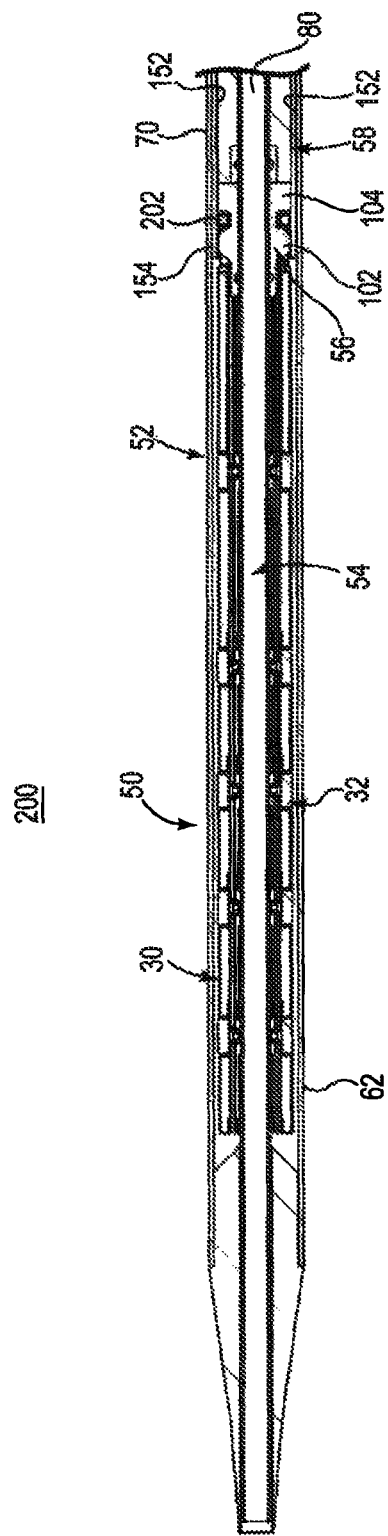
FIG. 7 is a cross-sectional view of a portion of a heart valve replacement system in accordance with the present disclosure, including the delivery device of FIG. 2A loaded with the prosthetic heart valve of FIG. 1B.

FIG. 7 illustrates a portion of a system 200 in accordance with the present disclosure for replacing (or repairing) a defective heart valve of a patient and including the stented prosthetic heart valve 30 within the delivery device 50. In the loaded state of the delivery device 50 in FIG. 7, the prosthetic heart valve 30 is crimped over the inner shaft assembly 54, with the delivery sheath assembly 52 located such that the capsule 62 surrounds and compressively retains the prosthetic heart valve 30 in the compressed arrangement shown thereby defining a loaded condition of the repair system 200. The hub 56 and the release sheath assembly 58 (referenced generally) are mounted to the inner support shaft 80, with the release sheath 154 being slidably directed over the cylindrical base 102 via deflection of the biasing members 152 (shown partially) in response to placement within the delivery sheath shaft 70. The release sheath 154 can be slidably supported along the flange 104 to better ensure desired positioning relative to cylindrical base 102. With this arrangement, then, a portion of the prosthetic heart valve stent frame 32 (e.g., posts 202) is captured to the hub 56 via the release sheath 154.

Figure 8A:
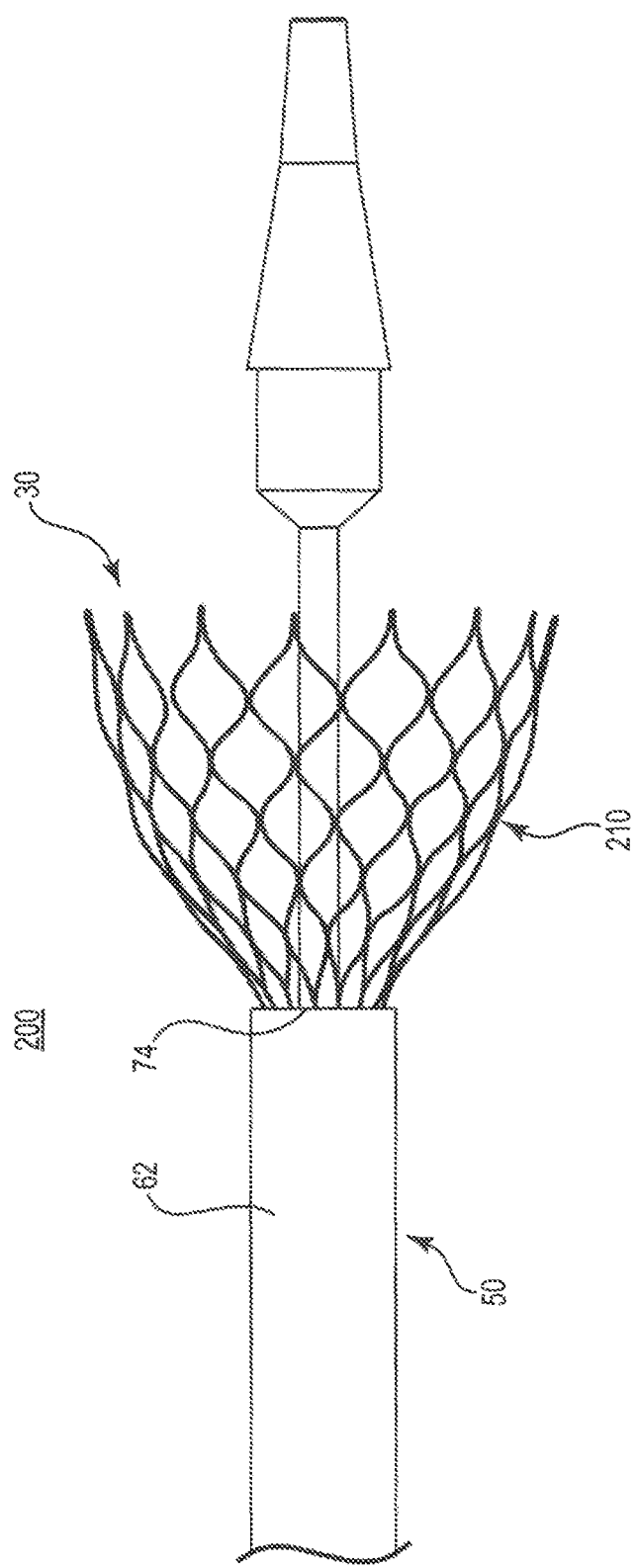
FIG. 8A is a side view of a distal portion of the system of FIG. 7 in a partially deployed state.
Figure 8B:
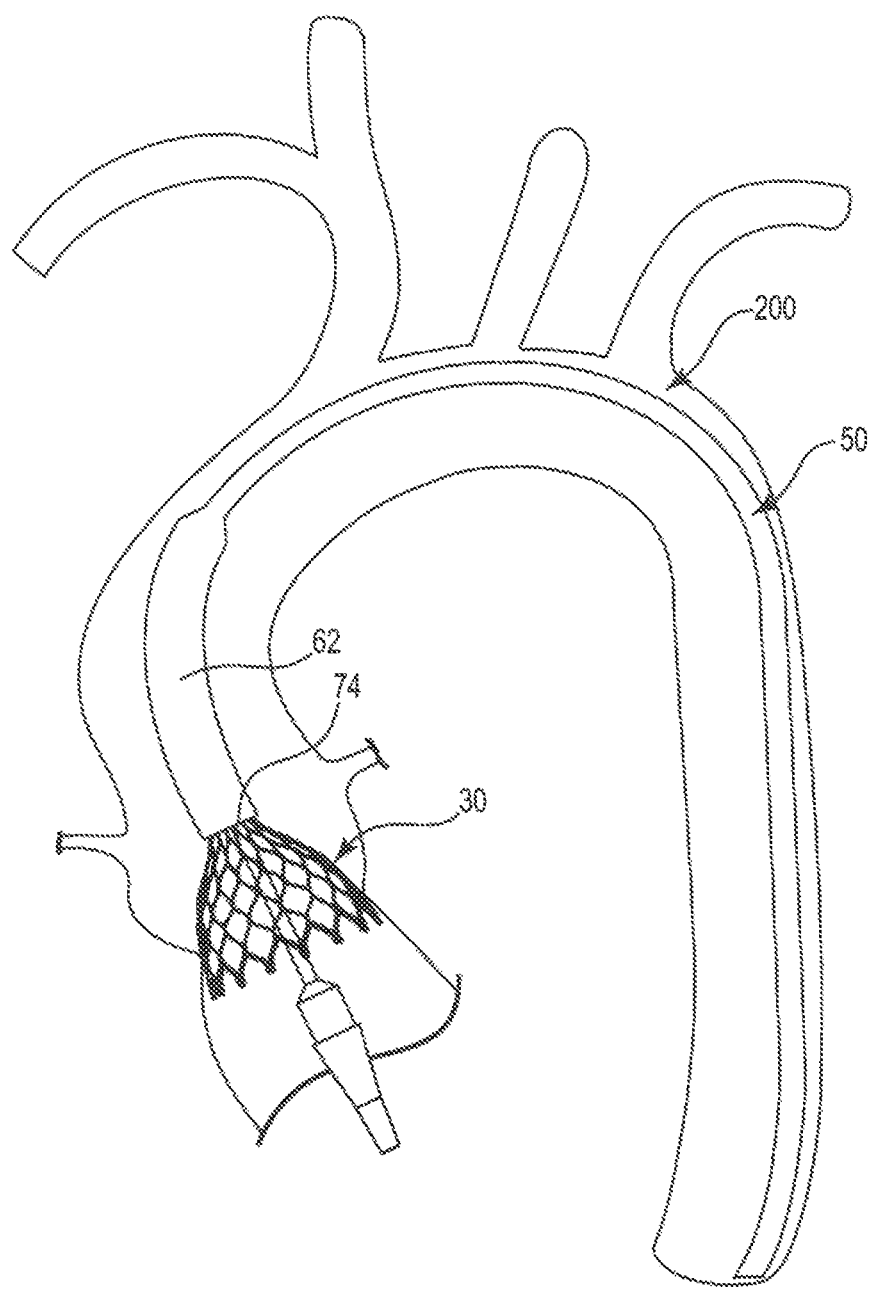
FIG. 8B illustrates delivery of the system of FIG. 8A within a patient's anatomy, including partial deployment of the stented prosthetic heart valve.

The loaded delivery device 50 can then be used to percutaneously deliver the prosthetic heart valve 30 to an implantation site, such as a defective heart valve. For example, the delivery device 50 is manipulated to advance the compressed prosthetic heart valve 30 toward the implantation site in a retrograde manner through a cut-down to the femoral artery, into the patient's descending aorta, over the aortic arch, through the ascending aorta, and approximately midway across the defective aortic valve (for an aortic valve repair procedure). The prosthetic heart valve 30 can then be partially or fully deployed from the delivery device 50. With either procedure, the capsule 62 (FIG. 2A) is proximally retracted or withdrawn from over the prosthetic heart valve 30. As generally reflected in FIG. 8A, at an initial stage of proximal retraction of the capsule 62, the distal end 74 is located approximately mid-length along the stented prosthetic heart valve 30. A distal region 210 of the prosthetic heart valve 30 is thus "exposed" relative to the distal end 74 of the capsule 62, and is allowed to self-expand. However, because the distal end 74 is distal the release sheath assembly 58 (hidden in FIG. 8A), a proximal region of the prosthetic valve 30 remains secured to the delivery device 50. FIG. 8B illustrates the system 200 percutaneously directed to a native valve and the delivery device 50 in a partially related state; as shown, the prosthetic heart valve 30 is partially deployed or expanded, yet remains connected to the delivery device 50.

Figure 9A:
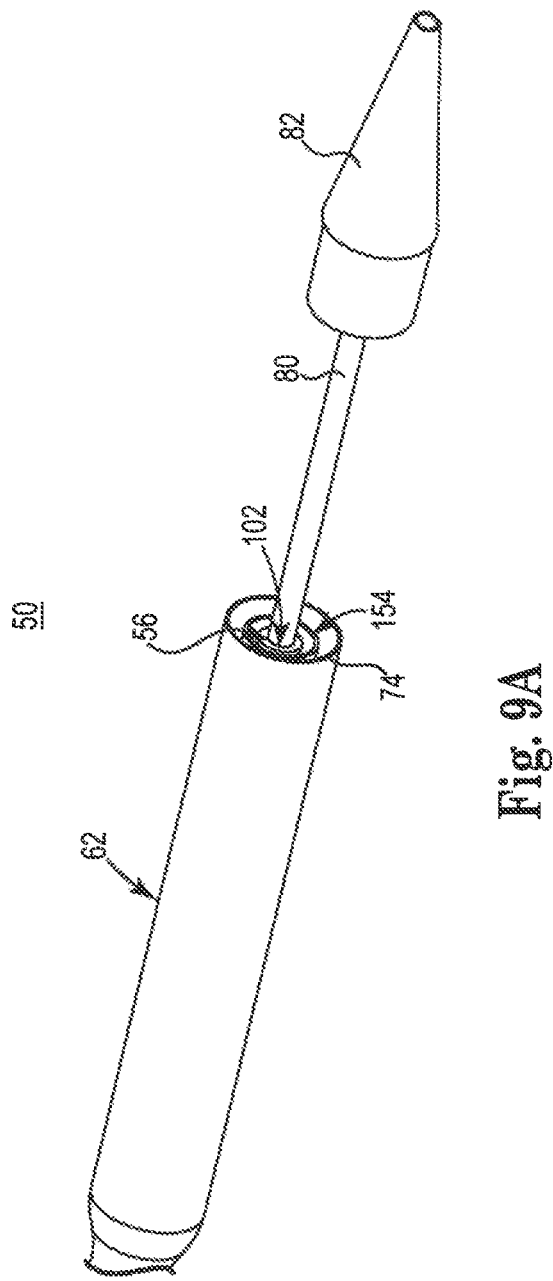
FIG. 9A is a simplified perspective view of the delivery device of FIG. 2A in a sequentially further stage of deployment.
Figure 9B:
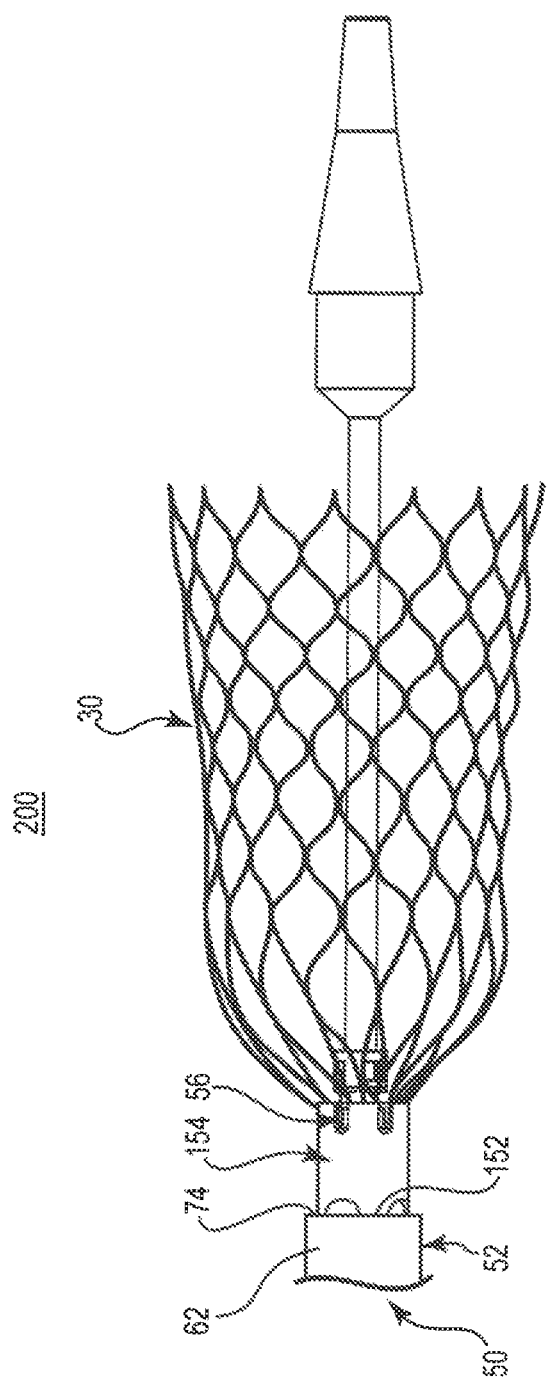
FIG. 9B is a side view of the system of FIG. 7 in a sequentially further state of partial deployment.

The delivery process continues by further retracting the delivery sheath assembly 52. As shown in FIG. 9A (in which the stented prosthetic heart valve 30 is omitted for purposes of clarity), proximal retraction has located the distal end 74 approximately over the hub 56 and the release sheath 154. Because the biasing members 152 (FIG. 6B) remains within the confines of the delivery sheath assembly 52, and thus in the deflected state, the release sheath 154 is held over the hub 56, thereby maintaining a secured connection of the stented prosthetic heart valve 30 to the delivery device 50. FIG. 9B illustrates an even further sequential retraction of the delivery sheath assembly 52, locating the distal end 74 immediately proximal the release sheath 154. However, because the biasing members 152 are still acted upon or constrained by the delivery sheath assembly 52, the stented prosthetic heart valve 30 remains secured between the release sheath 154 and the hub 56. As shown, in this partial deployment state, a substantial portion (e.g., 90%) of the stented prosthetic heart valve 30 has self-expanded toward the expanded condition.

In the stage of partial deployment of FIG. 9B (or in any other sequentially prior stage of partial deployment), the clinician can perform desired evaluations of the partially deployed prosthetic heart valve 30 relative to the implantation site. Notably, a substantial majority of the prosthetic heart valve 30 is in an expanded arrangement, including, for example, the inflow region and at least a portion of the outflow region. Thus, the valve replacement systems and delivery devices and methods of the present disclosure afford the clinician the ability to make an accurate estimate of the position of the prosthetic heart valve 30 relative to the implantation site. Under circumstances where the clinician determines that the prosthetic heart valve 30 should be repositioned, the capsule 62 can, in some constructions, be distally advanced back over the prosthetic heart valve 30, thereby resheathing or recapturing the prosthetic heart valve 30 and returning to the compressed arrangement. Alternatively, the delivery device 50 can incorporate other features to effectuate recapturing of the prosthetic heart valve 30.

Figure 10B:
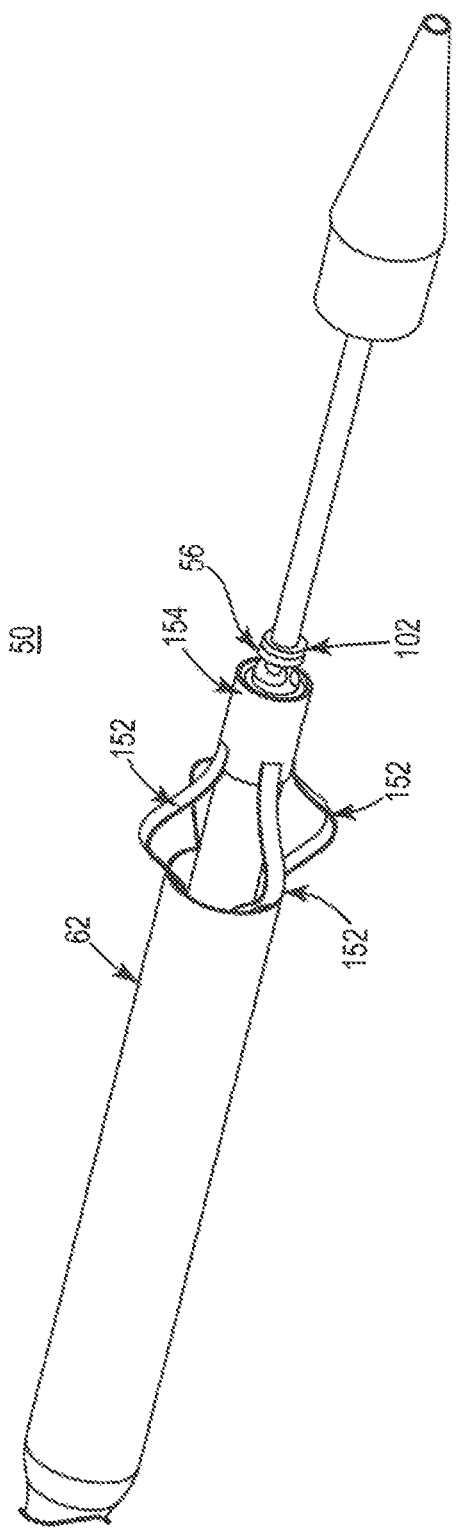

When full deployment of the prosthetic heart valve 30 from the delivery device 50 is desired, the capsule 62 is further proximally retracted over the biasing members 152. As shown in FIGS. 10A and 10B (the prosthesis 30 (FIG. 1A) being omitted from the views of FIGS. 10A and 10B for ease of explanation), as the biasing members 152 are sequentially released from the confines of the capsule 62, the biasing members 152 self-revert toward their natural state. This action, in turn, causes the biasing members 152 to proximally retract the release sheath 154 from the hub 56 (or at least the cylindrical base 102) as reflected by a comparison of the arrangement of FIG. 10A with that of FIG. 10B.

Figure 11A:
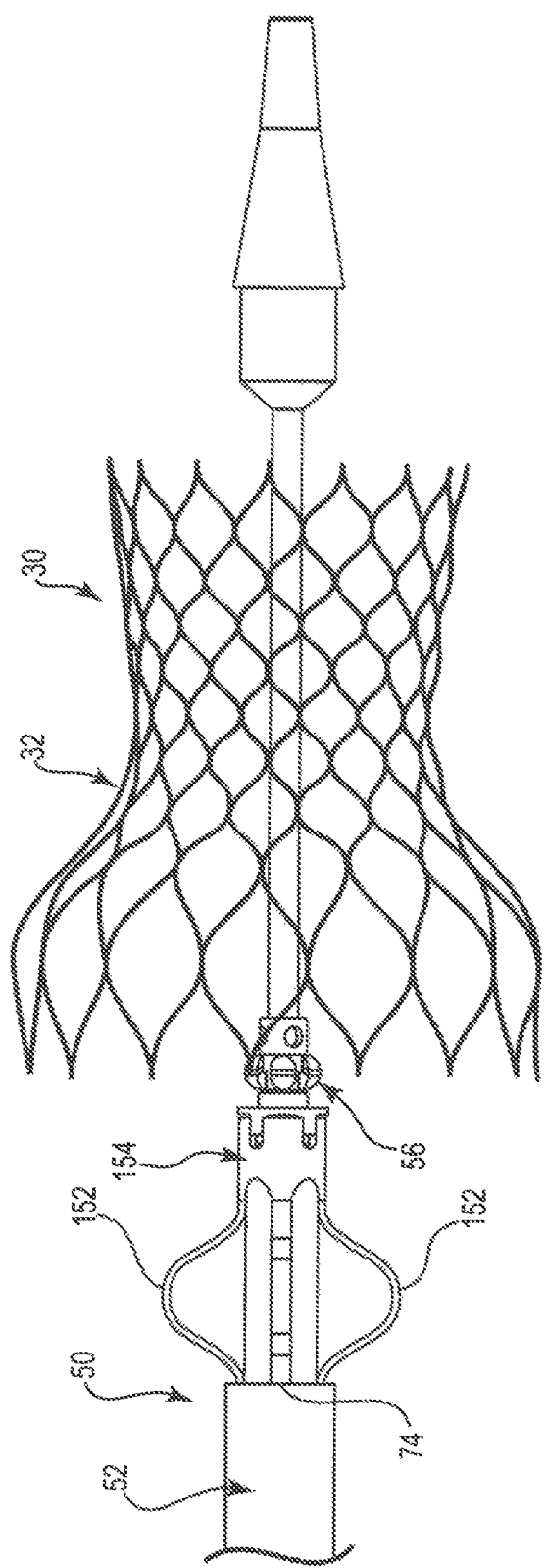
FIG. 11A is a side view of a portion of the system of FIG. 7 in a deployment state.
Figure 11B:
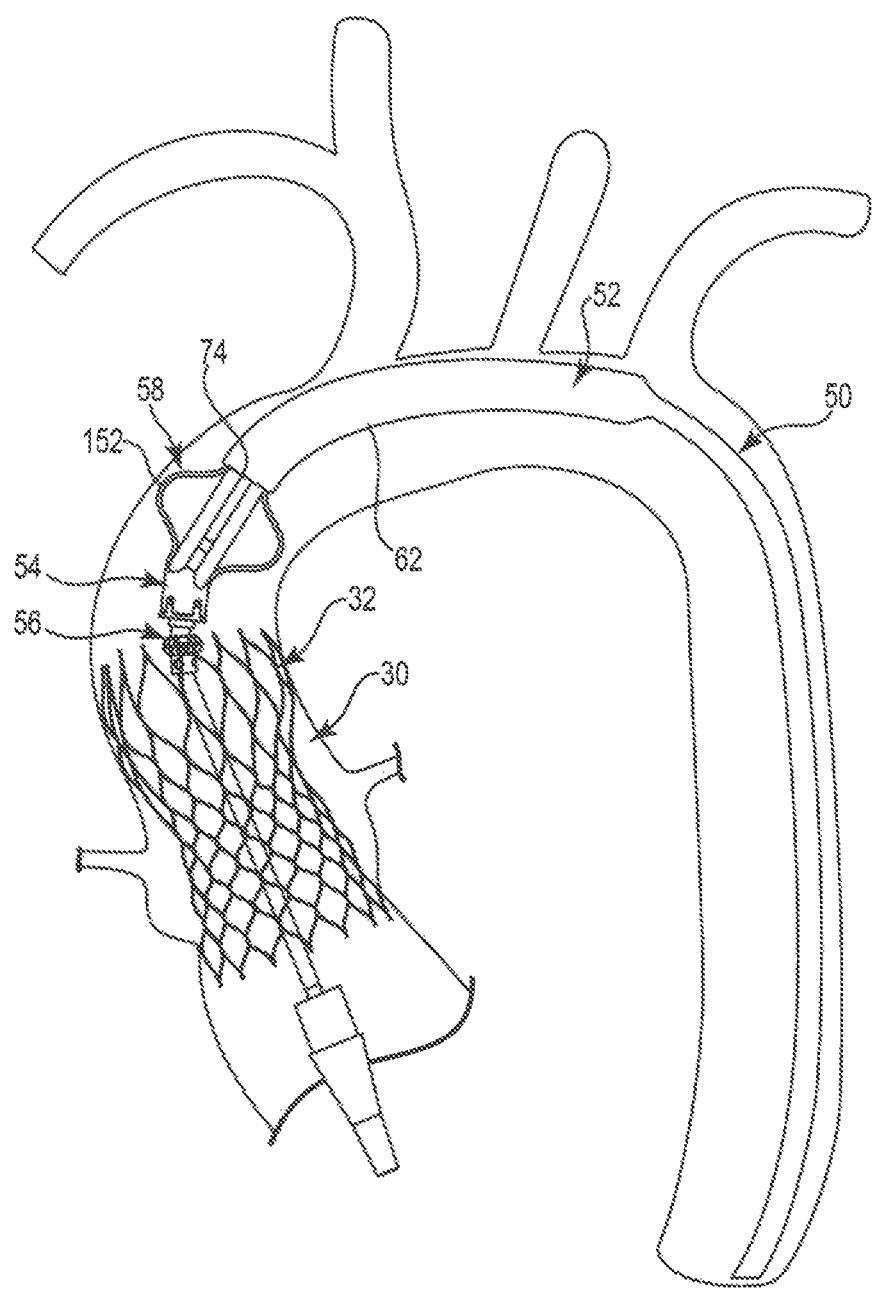
FIG. 11B illustrates, in simplified form, a location of the system of FIG. 7 relative to a patient's anatomy, including full deployment of the prosthetic heart valve from the delivery device and implantation to the native valve.

Retraction of the release sheath 154 relative to the hub 56 permits the stent frame 32 to fully release from the hub 56 as shown in FIGS. 11A and 11B. Once the release sheath 154 has self-retracted proximally beyond the stent frame 32, the prosthetic heart valve 30 fully releases from the delivery device 50 (e.g., due to self-expansion of the stent frame 32). FIG. 11B reflects that the released prosthetic heart valve 30 is now implanted to the native valve. The delivery device 50 can then be removed from the patient.

The delivery device 50 is configured so that the stent frame 32 of the prosthetic valve 30 will release from the delivery device 50 at a pre-designed step of the delivery sequence. This delivery device 50 thereby advantageously allows the user to entirely move an outer sheath from a valved stent prior to release of the stent from the delivery device 50. In addition, the device 50 allows the out flow portion of the valved stent to open or release so that the valve function can be determined prior to final release of the valved stent. Should the valve function be less than optimal and/or if it is desired to reposition the valve stent before it is completely released from the delivery device 50, the process steps described above can be performed in reverse order until the valve stent is sufficiently compressed within the sheath(s) that it can be moved to a different location or removed from the patient.

The delivery devices of the present disclosure provide for placement of a stent for replacement of an aortic valve, for example. Alternatively, the systems and devices of the present disclosure can be used for replacement of other valves and/or in other portions of the body in which a stent is to be implanted. When delivering a valved stent to replace an aortic valve, the delivery devices of the disclosure can be used with a retrograde delivery approach, for example, although it is contemplated that an antegrade delivery approach can be used, with certain modifications to the delivery device. With the systems described herein, full or partial blood flow through the valve can advantageously be maintained during the period when the valved stent is being deployed into the patient but is not yet released from its delivery device. This feature can help to prevent complications that may occur when blood flow is stopped or blocked during prosthetic valve implantation with some other known delivery devices. In addition, it is possible for the clinician to thereby evaluate the opening and closing of leaflets, examine for any paravalvular leakage and evaluate coronary flow and proper positioning of the valve within the target anatomy before final release of the valved stent.

Because it is often desirable to minimize the diameter of the system for percutaneous delivery of valved stents, the number of stent wires and corresponding extending elements can be designed or chosen to optimize the quality of the attachment between the stent frame and the delivery device, while providing a stent that has certain desirable characteristics when implanted in a patient.

The delivery devices shown and described herein can be modified for delivery of balloon-expandable stents, within the scope of the present disclosure. That is delivering balloon-expandable stents to an implantation location can be performed percutaneously using modified versions of the delivery devices of the disclosure. In general terms, this includes providing a transcatheter assembly which may include release sheaths and/or additional sheaths and/or collars including indentations and/or grooves, as described above. These devices can further include a delivery catheter, a balloon catheter, and/or a guide wire. A delivery catheter used in this type of device defines a lumen within which the guide wire is slidably disposed. Further, the balloon catheter includes a balloon that is fluidly connected to an inflation source. It is noted that if the stent being implanted is the self-expanding type of stent, the balloon would not be needed and a sheath or other retraining means would be used for maintaining the stent in its compressed state until deployment of the stent, as described herein. In any case, for a balloon-expandable stent, the transcatheter assembly is appropriately sized for a desired percutaneous approach to the implantation location. For example, the transcatheter assembly can be sized for delivery to the heart valve via an opening at a carotid artery, a jugular vein, a sub-clavian vein, femoral artery or vein, or the like. Essentially, any percutaneous intercostals penetration can be made to facilitate use of transcatheter assembly.

With the stent mounted to the balloon, the transcatheter assembly is delivered through a percutaneous opening (not shown) in the patient via the delivery catheter. The implantation location is located by inserting the guide wire into the patient, which guide wire extends from a distal end of the delivery catheter, with the balloon catheter otherwise retracted within the delivery catheter. The balloon catheter is then advanced distally from the delivery catheter along the guide wire, with the balloon and stent positioned relative to the implantation location. In an alternative embodiment, the stent is delivered to an implantation location via a minimally invasive surgical incision (i.e., non-percutaneously). In another alternative embodiment, the stent is delivered via open heart/chest surgery. In one embodiment of the stents of the disclosure, the stent includes a radiopaque, echogenic, or MRI visible material to facilitate visual confirmation of proper placement of the stent. Alternatively, other known surgical visual aids can be incorporated into the stent. The techniques described relative to placement of the stent within the heart can be used both to monitor and correct the placement of the stent in a longitudinal direction relative to the length of the anatomical structure in which it is positioned.

Once the stent is properly positioned, the balloon catheter is operated to inflate the balloon, thus transitioning the stent to an expanded condition.

The present disclosure has now been described with reference to several embodiments thereof. The foregoing detailed description and examples have been given for clarity of understanding only. No unnecessary limitations are to be understood therefrom. It will be apparent to those skilled in the art that many changes can be made in the embodiments described without departing from the scope of the disclosure. Thus, the scope of the present disclosure should not be limited to the structures described herein.

What is claimed is:

1. A delivery device for percutaneously deploying a stented prosthetic heart valve including a stent frame to which a valve structure is attached, the device comprising:
    a delivery sheath assembly terminating at a distal end and defining a lumen;
    an inner shaft slidably disposed within the lumen;
    a hub projecting from the inner shaft and configured to releasably receive a portion of a prosthetic heart valve stent frame; and
    a release sheath assembly disposed between the delivery sheath assembly and the inner shaft, the release sheath assembly including a release sheath slidably disposed about the inner shaft;
    wherein the delivery device is configured to provide a loaded state in which the delivery sheath assembly maintains a stented prosthetic heart valve over the inner shaft and coupled to the hub via the release sheath, and a deployment state in which the distal end of the delivery sheath assembly and the release sheath are withdrawn from the prosthetic heart valve to permit the prosthetic heart valve to release from the hub;
    and further wherein the release sheath assembly is configured to self-retract the release sheath proximally relative to the hub as the distal end of the delivery sheath assembly is proximally retracted relative to the release sheath.

2. The delivery device of claim 1, wherein the release sheath forms at least one longitudinal notch extending from a distal end of the release sheath.

3. The delivery device of claim 2, wherein the at least one longitudinal notch includes a plurality of circumferentially spaced longitudinal notches.

4. The delivery device of claim 1, wherein the release sheath assembly further includes a mounting base connected to the release sheath by at least one biasing member.

5. The delivery device of claim 4, wherein the at least one biasing member is a leaf spring-like body having opposing, first and second ends, and further wherein the first end is fixed to the release sheath and the second end is fixed to the mounting base.

6. The delivery device of claim 4, wherein the mounting base is fixed to the inner shaft proximal the hub and proximal the release sheath.

7. The delivery device of claim 6, wherein the release sheath assembly is self-transitionable from a deflected state to a normal state, and further wherein a longitudinal spacing between the release sheath and the mounting base in the deflected state is greater than a spacing in the normal state, and further wherein the loaded state includes the release sheath assembly forced to the deflected state via the delivery sheath assembly, and even further wherein the delivery device is configured to transition to the deployment state as the distal end of the delivery sheath assembly is proximally retracted along the leaf spring-like body whereby the release sheath assembly is allowed to self-transition toward the normal state and retract the release sheath from the hub.

8. The delivery device of claim 7, wherein the release sheath assembly includes two biasing members interconnecting the release sheath and the mounting base.

9. The delivery device of claim 8, wherein an outer diameter collectively defined by the biasing members in the normal state is greater than a diameter of the lumen of the delivery sheath assembly.

* * * * *